United States Patent
Doets et al.

(10) Patent No.: US 11,117,127 B2
(45) Date of Patent: Sep. 14, 2021

(54) MOLTEN METAL SAMPLER

(71) Applicant: HERAEUS ELECTRO-NITE INTERNATIONAL N.V., Houthalen (BE)

(72) Inventors: Jan Doets, Houthalen (BE); Guy Neyens, Houthalen (BE); Dries Beyens, Houthalen (BE); Jean-Paul Verhoeven, Houthalen (BE); Arne Potargent, Houthalen (BE)

(73) Assignee: HERAEUS ELECTRO-NITE INIERNATIONAL N.V., Houthalen (BE)

( * ) Notice: Subject to any disclaimer, the term of this patent is extended or adjusted under 35 U.S.C. 154(b) by 113 days.

(21) Appl. No.: 16/434,850

(22) Filed: Jun. 7, 2019

(65) Prior Publication Data

US 2019/0374937 A1   Dec. 12, 2019

(30) Foreign Application Priority Data

Jun. 12, 2018   (EP) ..................................... 18177315

(51) Int. Cl.
*G01N 1/12*        (2006.01)
*B01L 3/00*        (2006.01)
(Continued)

(52) U.S. Cl.
CPC ................. *B01L 3/502* (2013.01); *B22D 2/00* (2013.01); *G01N 1/125* (2013.01);
(Continued)

(58) Field of Classification Search
CPC ............ B01L 3/502; B01L 2300/0832; B01L 2400/0463; B22D 2/00; B22D 23/04; B22C 9/02; G01N 1/125
(Continued)

(56) References Cited

U.S. PATENT DOCUMENTS 3,589,199 A * 6/1971 Levin .................... G01N 1/1409
                                                      73/864.54
3,646,816 A   3/1972 Hance et al.
(Continued)

FOREIGN PATENT DOCUMENTS

EP      0002716 A2   7/1979
EP      3336511 A1   6/2018
(Continued)

OTHER PUBLICATIONS

Thomas R. Dulski, A Manual for the Chemical Analysis of Metals, ASTM, 1996.

*Primary Examiner* — Robert R Raevis
(74) *Attorney, Agent, or Firm* — Blank Rome LLP

(57) ABSTRACT

The present invention relates to a sampler for taking samples from a molten metal bath, particularly a molten iron, the sampler comprising:
  a carrier tube having an immersion end; and
  a sample chamber assembly arranged on the immersion end of the carrier tube, the sample chamber assembly comprising a cover plate and a housing, wherein the housing comprises:
  an immersion end having a first opening for an inflow conduit and an opposing end having a second opening for a gas coupler,
  a first face extending between the immersion end and the opposing end, the first face having a first depression proximate the immersion end and a second depression, the first depression being an analysis zone and the second depression being a ventilation zone, a portion of the analysis zone overlying a distribution zone which is in direct flow communication with the first opening and configured to receive the molten steel from the inflow conduit, (Continued)

wherein the first depression having a cross sectional circle segment profile along a central longitudinal axis that is concavely or triangularly shaped, wherein the cover plate and the housing are configured to be assembled together to form a sample cavity including the distribution zone, the analysis zone and the ventilation zone, such that an analysis surface of a solidified steel sample formed within the sample cavity lies in a first plane, and wherein the first and second openings are spaced apart from the first plane.

The invention also relates to a sampler for taking samples from a molten metal bath, particularly a molten iron.

13 Claims, 4 Drawing Sheets

(51) Int. Cl.
  B22D 2/00 (2006.01)
  *B22C 9/02* (2006.01)
  *B22D 23/04* (2006.01)

(52) U.S. Cl.
  CPC ............... *B01L 2300/0832* (2013.01); *B01L 2400/0463* (2013.01); *B22C 9/02* (2013.01); *B22D 23/04* (2013.01)

(58) Field of Classification Search
  USPC ............................. 73/863.51, 864.53–864.59
  See application file for complete search history.

(56) References Cited

U.S. PATENT DOCUMENTS

| | | | | |
|---|---|---|---|---|
| 3,915,014 | A | * 10/1975 | Judge | ............... G01N 1/1409 73/864.54 |
| 4,007,641 | A | 2/1977 | Kelsey | |
| 4,046,016 | A | * 9/1977 | Hackett | ............... G01N 1/125 73/864.57 |
| 4,125,024 | A | 11/1978 | Vierbicky | |
| 4,211,117 | A | 7/1980 | Cure | |
| 4,401,389 | A | 8/1983 | Theuwis | |
| 4,453,424 | A | 6/1984 | Hackett | |
| 4,499,777 | A | * 2/1985 | Hackett | ............... G01N 1/125 73/864.56 |
| 4,541,292 | A | 9/1985 | Clay | |
| 5,415,052 | A | 5/1995 | Baerts | |
| 9,128,013 | B2 | 9/2015 | Song et al. | |
| 2014/0318276 | A1 | 10/2014 | Cappa et al. | |

FOREIGN PATENT DOCUMENTS

| | | |
|---|---|---|
| EP | 3336512 A1 | 6/2018 |
| EP | 3336513 A1 | 6/2018 |
| EP | 3336514 A1 | 6/2018 |
| FR | 2413653 A1 | 7/1979 |
| GB | 1456353 A | 11/1976 |
| JP | S5835461 A | 3/1983 |
| KR | 20140130044 A | 11/2014 |
| RU | 2155948 C2 | 9/2000 |
| RU | 2569417 C1 | 11/2015 |
| SU | 1161840 A1 | 6/1985 |

* cited by examiner

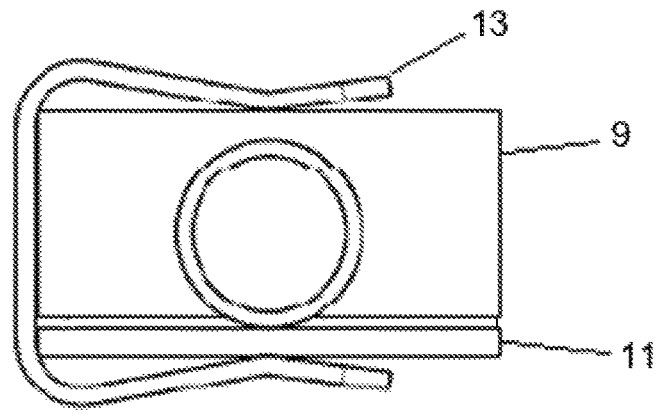
FIG. 2
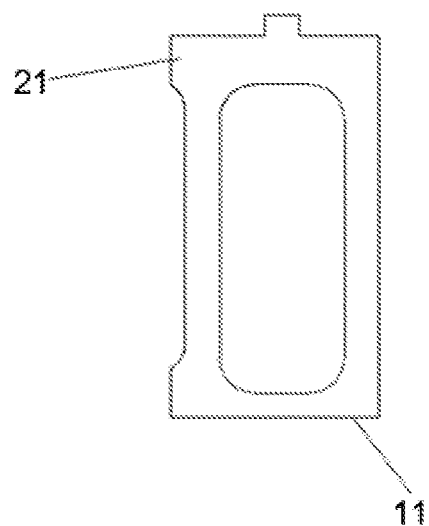 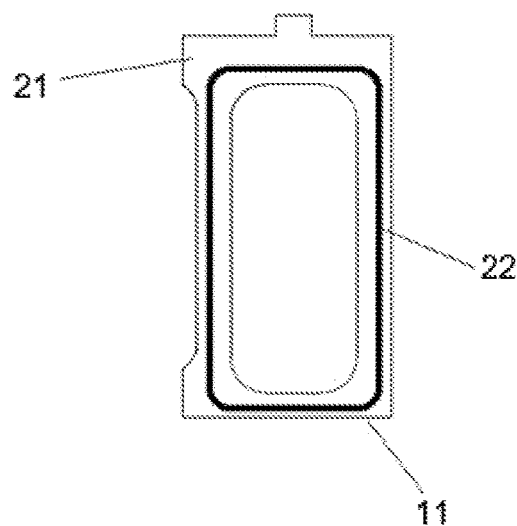
FIG. 3a  FIG. 3b

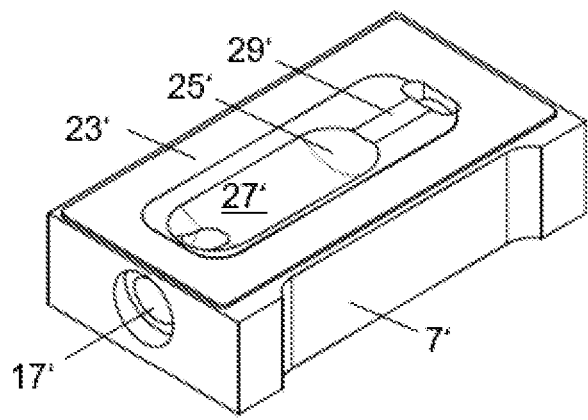 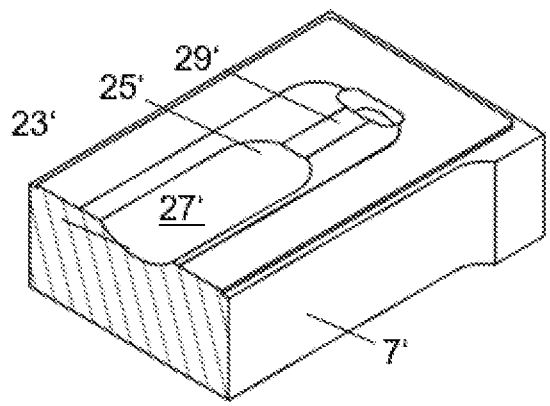
FIG. 4a                              FIG. 4b
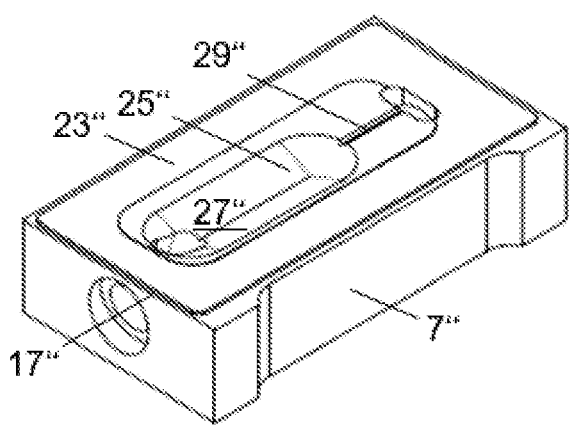 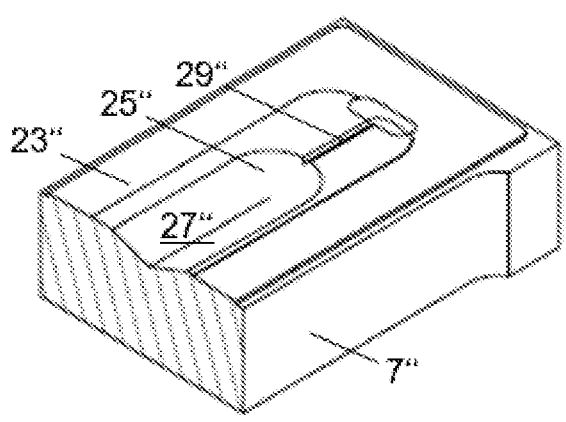
FIG. 5a                              FIG. 5b

MOLTEN METAL SAMPLER

CROSS REFERENCE TO RELATED APPLICATION

This application claims the benefit of Europe Application No. 18177315.1, filed Jun. 12, 2018, the entire contents of which are incorporated by reference herein.

FIELD OF THE INVENTION

The invention relates to a sampler for taking samples from a molten metal bath, particularly from a molten steel bath or molten iron bath.

BACKGROUND OF THE INVENTION

During the processing of metals in their molten state, it is necessary to obtain a representative sample of the molten metal at various stages of the process, for example, for the analysis or evaluation of either the chemical composition or the metallographic structure of the sample. Different methods for analyzing molten metals during manufacturing and further processing are known in the art.

Historically, the composition of a solidified metal sample is often determined using arc spark-optical emission spectroscopy, spark-OES, equipment. Spark-OES systems are generally the most effective systems for determining the chemical composition of a metal sample and for controlling the processing of molten metals due to their rapid analysis times and inherent accuracy. Thus, spark-OES analysis is typically used during molten metal processes for controlling the progress of molten metal production.

Spark-OES involves exciting atoms of a target sample of which knowledge of the composition is desired, and examining the wavelength of photons emitted by atoms during transition from an excited state to a lower energy state. Each element in the periodic table emits a characteristic set of discrete wavelengths when its atoms return from an excited state to a lower energy state. By detecting and analyzing these wavelengths, the elemental composition of a sample can be determined in accordance with a calibration curve, thereby showing the relationship between the spectral intensity ratio (i.e., absolute radiation power of an element/absolute radiation power of the base metal) and the concentration of the element in the standard sample.

The spectral light may be produced by irradiation with electromagnetic radiation, such as by a laser or x-rays, but is generally produced for spark-OES by a short spark produced by a spark generator incident upon the target of which knowledge of its elemental composition is desired. In this case, the target is the metal sample. Spark generators, their intensity and their pulse regime vary according to the specific spark-OES equipment. Irrespective of the spark energy input, the accuracy and reliability of such emission spectrometers has been known to be dependent on the accuracy and quality of the detector and optics used to receive the radiation emitted from the sample and the homogeneity of the metal sample itself.

Broadly speaking, the spark-OES analysis procedure begins with the conductive metal sample being positioned with its analysis surface face down on a predetermined region of the stage of the spark-OES instrument, namely an optical emission spectrometer. More particularly, the sample is positioned so as to span and close the analysis opening of the spectrometer and an anode nearly abuts the analysis surface of the sample. Once the desired positioning of the sample and proximity of the anode and analysis surface is achieved, a spark is discharged between the anode and the conductive metal sample which is electrically connected to the spectrometer stage. This connection is, in most cases, made by gravitational force in combination with a small load. The analysis opening on the optical emission spectrometer is typically around 12 mm wide. This distance avoids that a spark arcs between the anode and the instrument housing. The optical detector receives the emitted light from the excavated material of the sample surface. The spark chamber, formed in part by the space between the anode and the metal sample, is continuously purged with argon or other inert gas in order to avoid air ingress which would lead to erroneous analysis values.

In order to lay flat upon the analysis opening of the spectrometer, the metal sample cannot have any extensions and the analysis surface of the metal sample must be smooth. There can be no part of the sample or sample housing which will break the plane of the analysis surface. The sample must span the analysis opening of the spectrometer and be of sufficient flatness to facilitate inert gas purging of the spark chamber and present a contiguous sample surface toward the anode.

The procedures and processes to obtain a representative analysis of metals are well known in the art as described in In Dulski, T. R. A Manual for the Chemical Analysis of Metals, ASTM International, 1996. Until now, it has been generally believed that the metal sample and the instrumentation used for its analysis are independent of each other and, as such, one does not influence the other.

Conventional sampling devices which provide a coupon or disc of solid metal for use in spectrographic analysis are known. The geometric shape and dimensions of the solidified metal coupons obtained by such sampling devices will sometimes be specific to the type of metal or metallographic need. A general category of samples that are obtained by immersion devices for spark-OES analysis are samples having a disc or oval shape and a diameter or long length of 28 to 40 mm. Most commonly, such samples have a diameter or long length of about 32 mm and a thickness of 4 to 12 mm. Some samplers, commonly known as lollipop samplers, may produce a differently shaped sample, ranging from round to oval or longer, according to the requirements of the user, but most samples still have a diameter or long length of about 32 mm. Other samplers, commonly known as dual thickness samplers, combine two thicknesses within the same sample.

Typical sampling devices designed to obtain samples of molten metal for analysis by spark-OES include a sample chamber or mold cavity configured to be filled with molten metal upon immersion of the sampling device into the molten metal bath. The molds which delineate the mold cavity or sampling chamber are typically either a two-part clam shell type arrangement or a ring covered on its upper and lower sides by flat plates. Once the sample of metal is solidified, the molds are discarded and the sample is cooled, transported to the laboratory, analysis surface is grinded, a further cooling step upon which the sample is transported to the spark-OES for analysis.

U.S. Pat. No. 3,646,816 describes this type of expendable immersion sampler, in which both flat surfaces of a disc-like sample are formed by chill-plates to achieve more rapid freezing and a pair of smoother surfaces which require less clean-up prior to analysis. Other prior art patents, such as U.S. Pat. No. 4,211,117, relate to a similar concept, while U.S. Pat. Nos. 4,401,389 and 5,415,052 provide examples of this metallurgical sample being combined with other sensors, one of which could be a temperature measuring sensor.

Samples produced by conventional sampling devices have a diameter of about 32 mm in a direction parallel to the spectrometer opening and a thickness of 4 to 12 mm in a direction perpendicular to the spectrometer opening. It has been found that a solidified sample of conventional thicknesses requires surface grinding from 0.8 to 5 mm of the as-cast surface, in order to achieve an analysis surface which is free from metal and non-metallic segregation. Conventional samples can only achieve this surface state after preparation processes to produce a geometry that is typically at least 28 mm in diameter in a direction parallel to the spectrometer opening and has a thickness which is typically less than 12 mm in a direction perpendicular to the opening. This after-preparation geometry is often handled by pre-analysis preparation equipment that mechanically grinds the sample surface and is also convenient for handling by robotic manipulators which advance the sample from preparation through analysis and removal to await the next sample.

Eliminating the need for surface preparation shortens the analysis time and is economically favorable to the metal producer. Various solutions to this problem are described in EP3336513A1, EP3336514A1, EP3336512A1, and EP3336511A1. These documents relate to Direct Analysis, DA, samplers which are a newly developed type of molten metal immersion sampler, which produce DA samples. DA samples do not require any kind of surface preparation before being analyzed, and thus can result in significant economic benefit both in terms of the availability of timely chemistry results as well as laboratory time savings by utilizing the spark-OES analysis method. In particular, the aforementioned prior art describes a uniform filling of the sample cavity and rapid chilling of the molten metal sample, such that the entire sample section presented for analysis freezes uniformly and without surface oxidation. The heat content of the solidifying metal is reduced to bring the sampled metal to near room temperature before it is removed from the sampling chamber molds. The obtained samples have smaller volumes than that described in the prior art, so that unnecessary large sample volumes don't preclude rapid solidification of the molten metal sample. Hence, the samples described in EP3336513A1, EP3336514A1, EP3336512A1, and EP3336511A1 can be analyzed by spark-OES without surface preparation and thereby potential economic benefit is gained.

However, the DA samples obtained with the aforementioned prior art DA samplers still have shortcomings such as high temperatures of the samples, poor fixation of the samples in the sample chamber, contamination of the DA sample with unwanted elements and/or uncontrolled filling partial filling, or early filling.

Therefore, the invention aims at providing a solution for improving the quality of DA samplers, and hence the quality of accordingly obtained DA samples.

It is an objective of the present invention to provide an improved sample chamber and to provide a sealing member for sealing the sample chamber that does not contaminate the sample and also allows to create a sample chamber with minimum outer dimensions.

SUMMARY OF THE INVENTION

The invention provides a sampler for taking samples from a molten metal bath, particularly a molten iron, the sampler comprising:

a carrier tube having an immersion end; and
a sample chamber assembly arranged on the immersion end of the carrier tube, the sample chamber assembly comprising a cover plate and a housing, wherein the housing comprises:
an immersion end having a first opening for an inflow conduit and an opposing end having a second opening for a gas coupler,
a first face extending between the immersion end and the opposing end, the first face having a first depression proximate the immersion end and a second depression, the first depression being an analysis zone and the second depression being a ventilation zone, a portion of the analysis zone overlying a distribution zone which is in direct flow communication with the first opening and configured to receive the molten steel from the inflow conduit,
wherein the first depression having a cross sectional circle segment profile along a central longitudinal axis that is concavely or triangularly shaped,
wherein the cover plate and the housing are configured to be assembled together to form a sample cavity including the distribution zone, the analysis zone and the ventilation zone, such that an analysis surface of a solidified steel sample formed within the sample cavity lies in a first plane, and
wherein the first and second openings are spaced apart from the first plane.

Advantageously, due to the hollow inward shaped indentation the temperature of the sample can be minimized, while the thickness of the sample can be increased. In particular, the mass of the sample is reduced by creating a circle segment or triangle shaped cross section of the sample. This allows to reduce the sampled mass with up to 50% without increasing the effect of heating during sparking. The applicant could conclude that the sample temperature when offered to the spectrometer and the heat dissipation capability of the sample are important for the analysis accuracy. Although the sample is offered to the spectrometer in its housing the applicant could conclude that the basic sample thickness at the spark-position is influencing the accuracy of the analysis. The mass of the housing helps to equalize the sample temperature over the total analysis period, i.e. at least 2 spark analysis results are compared to validate the output. Furthermore, the length of the sample can be minimized and the sample has an excellent fixation in the first depression.

In one embodiment, the second depression is having a cross sectional circle segment profile that is concavely or triangularly shaped, and/or wherein the depth of the second depression continually increases towards the first depression. The sparks are intended to be focused on the maximum depth axis of the sample. It is considered that a maximum depth of 4 mm can be used for analysis with a sample width of 10 mm. Increasing the sample width should lead to a reduction of the maximum depth of the sample accordingly. This can be explained by the reduced cooling capacity of the sample housing locally. The concave or triangle shaped sample and ventilation zone also reduces the formation of flash, formed in the small gap between the sample cavity mold and cover. Specifically, flash formed in the ventilation zone can cause cracks in the sample and generate loose parts of the sample that might fall in the spectrometer analysis chamber, causing electrical shortcuts.

In another embodiment, the first depression is having a substantially uniform depth, or an increasing depth towards the second depression or towards the immersion end.

Also, in another embodiment, the sample cavity and the first and second openings are aligned along a common longitudinal axis.

In yet another embodiment, the analysis zone, distribution zone and ventilation zone are structured as a plurality of contiguous segments, each segment having a length to depth ratio, a sum of the length to depth ratios of the plurality of segments being greater than 25.

In one embodiment, the distribution zone, analysis zone and ventilation zone are structured as a plurality of contiguous segments, each segment having a length to depth ratio, the length to depth ratios of the segments successively increasing as the distance from the first opening increases.

In another embodiment, there are no increases in a width dimension of at least a portion of the analysis zone in a flow direction of the molten steel which extends from the end of the distribution zone toward the second opening.

In one embodiment, a total length of the analysis zone and the ventilation zone is between 20 and 50 mm, preferably 30 mm long.

In another embodiment, a cross-sectional area of the analysis zone gradually tapers in the flow direction of the molten steel, and/or
wherein a cross-sectional area of the ventilation zone gradually tapers in the flow direction of the molten steel.

In one embodiment, the sampler comprising a measuring head supported on the carrier tube and adapted to accommodate at least parts of the sample chamber.

The invention also provides a sampler for taking samples from a molten metal bath, particularly a molten iron, the sampler comprising:

a carrier tube having an immersion end;

a sample chamber assembly arranged on the immersion end of the carrier tube, the sample chamber assembly comprising a cover plate and a housing, wherein the cover plate comprising a sealing member configured to provide a substantially gas tight seal between the cover plate and the housing, wherein the sealing member consist of an essentially non-contaminating material for the samples in the sample chamber.

Here, the term "sampler" can be used to refer to a Direct Analysis sampler as described above. The term "Substantially Gas Tight" means that the seal or joint may be completely gas tight or gas tight to a large degree. Also, "Essentially Non-Contaminating" means that the non-contaminating material will not cause segregation of unwanted elements from said material into the samples or deposit on the analysis surface, i.e. either no unwanted elements at all, or prevents segregation to a large degree, where only traces of unwanted elements can be detected.

Advantageously, the sealing member prevents dirt to stick to either the cover plate or the housing, which would contaminate the surface of a spectrometer and influence the ongoing analysis and even the following analyses.

In one embodiment, the sealing member, preferably a gasket, having a thickness of 0.05 mm to 0.2 mm, preferably a thickness of 0.12 mm. In further embodiments, other thicknesses can be used, but thicknesses which are far removed from the above stated range are complicated in practice. Also, the sealing member could be, for example, realized as an O-ring.

In another embodiment, the non-contaminating material is a non-impregnated paper material.

In one embodiment, the non-contaminating material is a pre-form comprising a synthetic or natural elastomer, wherein the deformable material is pre-cured to a temperature of at least 100° C., preferably more than 120° C.

In another embodiment, the sealing member is attached to the cover plate by bending at least one section of the sealing member around the cover plate, in particular, over a length of at least 3 mm.

In one embodiment, the sealing member is attached to the cover plate by a low-tack pressure-sensitive adhesive material that is essentially non-contaminating for the samples in the sample chamber. Said adhesive material can be applied over a part of the surface and is preferably applied to the cover part of the sampler or to the sealing member side facing the cover plate. It is desired that the adhesive material is applied away from the edge (cutting sides) of the sealing member. In case the adhesive is applied in the space between the sampler body and the cover plate it is best practice to apply the adhesive as far away from the inflow conduit as possible. The target of the bending of the sealing member and/or use of the adhesive is to make sure that the sealing member will be removed together with the cover plate during the opening of the sample chamber assembly and prevents that the sealing member will stay connected to the body part of the sampler, preventing analysis on the spark-OES instrument.

In one embodiment, the sampler comprises a measuring head supported on the carrier tube and adapted to accommodate at least parts of the sample chamber.

BRIEF DESCRIPTION OF THE DRAWINGS

The following schematic drawings show aspects of the invention for improving the understanding of the invention in connection with some exemplary illustrations, wherein

FIG. 2 shows a schematic view of a sample chamber assembly according to an embodiment of the invention;

FIGS. 3a, 3b show schematic top views of a cover plate and a sealing member according to embodiments of the invention;

FIGS. 4a, 4b a schematic view of a housing of a sample chamber assembly according to an embodiment of the invention; and FIGS. 5a, 5b a schematic view of a housing of a sample chamber assembly according to another embodiment of the invention.

DETAILED DESCRIPTION

Figure 1:
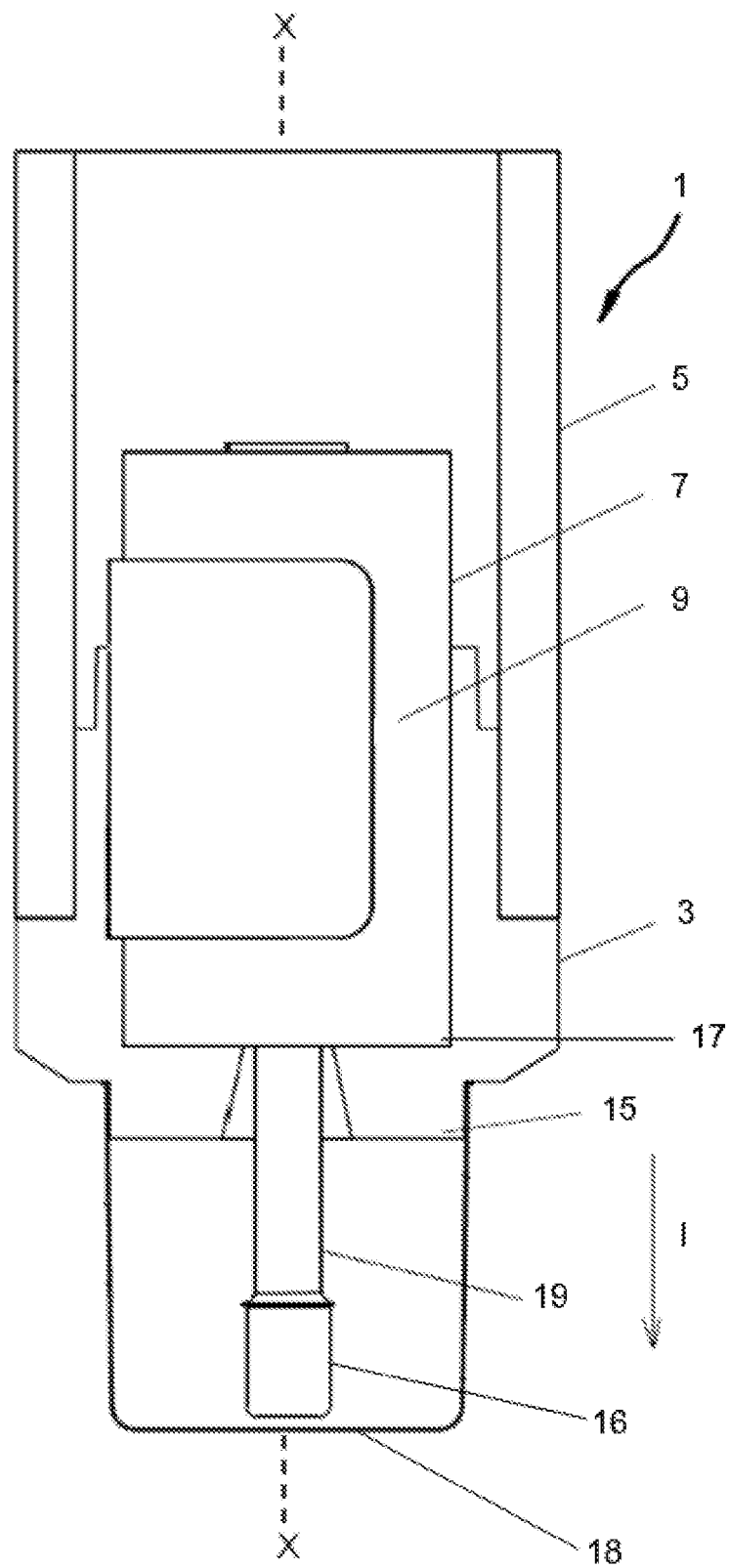
FIG. 1 shows a schematic view of a sampler according to embodiments of the invention.

FIG. 1 shows a sampler 1 for taking samples from a molten metal bath. The sampler 1 is suitable for immersion in and sampling of molten steel. The shown sampler 1 comprises a measuring head 3 which can be made of resin bonded silica sand. The measuring head 3 is supported on a carrier tube 5, which can be a paper carrier tube. In use, a probe holder or lance (not shown) is preferably inserted into the interior volume of the carrier tube 5 to provide the mechanical action necessary to submerse the measuring head 3 below the surface of a bath of molten metal (not shown) in the immersion direction I.

The measuring head 3 comprises a sample chamber assembly 7 for collection and retrieval of a sample of molten metal. The sample chamber assembly 7 as shown is a two-part sample chamber composed of a housing 9 and cover plate 11 as shown in more detail in FIG. 2. The housing 9 is preferably formed of one or more materials which are good thermal and electrical conductors, such as, but not limited to, aluminum, copper and other metals having similar thermal and electrical conductivity properties for being electrically coupled to the retrieved metal sample. The housing and the cover plate 9, 11 of the sample chamber assembly 7 can be held together by a clamp 13, as better shown in FIG. 2, with a compression force sufficient to resist a tendency of the two parts 9, 11 of the sample chamber 7 assembly to separate due to the force of molten metal flowing into and filling the sample chamber assembly 7 and the force during the purging phase prior to the filling of the sample. The clamp 13 can be a metal clamp.

FIG. 1 also shows the measuring head 3 having a first end and an opposing second end. The first end of the measuring head 3 corresponds to an immersion end 15 of the measuring head 3. The second end of the measuring head 3 is configured to face the lance or probe holder. Also, the sample chamber assembly 7 has a first end and an opposing second end. The first end of the sample chamber assembly 7 corresponds to an immersion end 17 of the sample chamber assembly 7. It will be understood by those skilled in the art that the phrase "immersion end" means the end of the body which is first immersed into molten metal. The first end of the sample chamber assembly 17 is attached to an inflow conduit 19, where the inflow conduit is received at an opening in the housing 9. The inflow conduit 19 enables the flow of molten metal from the molten metal bath into the sample chamber assembly 7. Thus, molten metal is introduced into the sample chamber assembly 7 in a direction opposite the immersion direction I parallel to the longitudinal axis X of the sample cavity. The inflow conduit 7 can be made of a quartz material, more preferably a fused quartz material.

The sample chamber assembly 7 as described above and shown in the figures needs to be pre-pressurized before filling. This pressure build-up is needed to obtain a defined filling moment after the unit has been sent to the required depth. Keeping the sampler during a waiting time in this position before starting the filling of the sample chamber assembly 7 allows the liquid bath to become homogeneous. This is needed to allow a protection cap 18 and inlet cap 16 of the sampling unit to burn and/or melt and the metallic components coming from the caps 16, 18 to disperse in the melt.

In order to create a pressure build-up in the sample chamber assembly 7, the sample chamber assembly 7 needs to be sealed. The maximum leak can be determined based on the applied flow of inert gas. It is considered a benefit to allow a minimum flow of gas. This gas removes the air/oxygen entrapped in the sample chamber assembly 7 during storage. In case the sample assembly chamber assembly 7 shows leaks between the parts that define the sample chamber assembly 7 there is a risk of uncontrolled filling, partial filling or early filling. All these failure modes will lead to samples that can't be analyzed or deliver deviating analysis results. The sample chamber assembly 7 needs to be pre-pressurized to a level that exceeds the ferrostatic pressure level.

Therefore, the sealing member 21 shown in FIGS. 3a and 3b consists of an essentially non-contaminating material for the samples in the sample chamber assembly such as a non-impregnated paper material, or a pre-form comprising a synthetic or natural elastomer that is pre-cured to a temperature of at least 100° C., preferably more than 120° C. This pre-curing temperature should be seen in combination with the maximum temperature of the sample chamber assembly during the total process. The lower the temperature of the sample chamber assembly, the lower the pre-curing temperature will be. The higher the temperature of the sample chamber assembly, the higher the required pre-curing temperature will be. These materials have the capability to absorb dirt such as tar formed during the heating of the sensor in the bath.

For practical purposes of assembly, the cover plate 11 can have approximately the same width and length as the housing 9. The cover plate 11 preferably has a thickness between 1 mm and 5 mm. The first side of the cover plate 11 is configured to face the housing 9. The sealing member 21 is provided on one side of the cover plate 11 so as to be positioned between the housing 9 and cover plate 11 in the assembled configuration of the sample chamber assembly.

In the shown embodiment, the sealing member 21 is a gasket dimensioned so as to encompass or surround a ridge in an assembled configuration of the sample chamber assembly. The sealing member 21 can be attached to the cover plate 11 by a low-tack pressure-sensitive adhesive material that is essentially non-contaminating for the samples in the sample chamber assembly, or alternatively by bending at least one section of the sealing member 21 around the cover plate 11, in particular, over a length of at least 3 mm.

Figure 3C:
FIGS. 3c-f show schematic side views of a cover plate and a sealing member according to embodiments of the invention.

FIG. 3c shows a side view of the cover plate 11 with the sealing member 21 arranged in a loose manner.

Figure 3D:
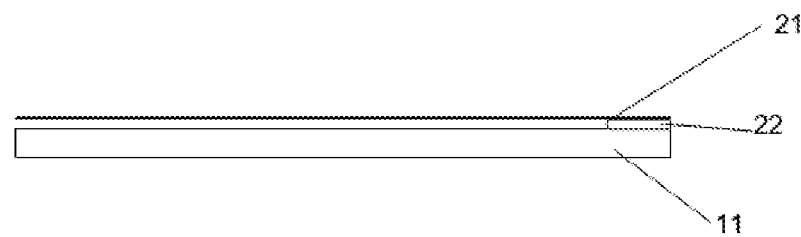

FIG. 3d shows a side view of the cover plate 11 with the sealing member 21 arranged with adhesive 22.

Figure 3E:
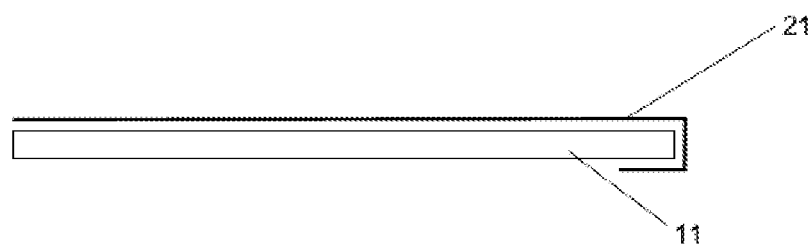

FIG. 3e shows a side view of the cover plate 11 with the sealing member 21 folded over onto the outer surface of the cover plate 11.

Figure 3F:
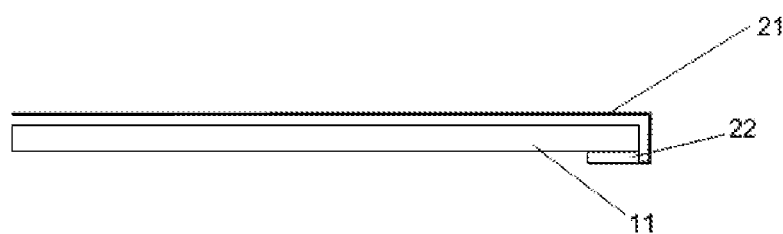

FIG. 3f shows a side view of the cover plate 11 with the sealing member 21 folded over onto the outer surface of the cover plate 11 and fixed with adhesive 22 onto the outer surface of the cover plate 11.

FIG. 4a shows a schematic view of a housing 7' of a sample chamber 25' according to an embodiment of the invention, and FIG. 4b shows a cut through the housing 7' shown in FIG. 4a. The first face 23' shown in the figures is an analysis face, meaning it is the geometric side of the housing 7' in which the sample is collected and which is thus configured to be positioned face down upon the stage of optical emission spectrograph during analysis.

As it can be seen the first face 23' extends between the immersion end 17' and the opposing end of the housing 7', and of the sample chamber 25', respectively. At the second end opposite the immersion end 17' of the sample chamber 25', there is provided a gas port which is preferably wholly contained within the housing 7'.

FIGS. 4a and 4b also show that the first face 23' is hollowed out to form different regions or zones of the sample chamber 25' for ventilation and the collection of molten metal. Therefore, the first face 23' comprises various depressions which collectively form the sample cavity of the sample chamber 25', as follows: A first depression 27' being an analysis zone, and a second depression 29' being a ventilation zone. A portion of the analysis zone overlying a distribution zone which is in direct flow communication with the opening at the immersion end 17' and configured to receive the molten steel from the inflow conduit.

The first depression 27' is defined by an elongated concavely shaped indentation or depression formed in the first face 23' of the housing 7'.

Due to the concavely shaped indentation the temperature of the sample can be minimized, while the thickness of the sample can be increased. In particular, the mass of the sample is reduced by creating circle segment-shaped sample. This allows to reduce the sampled mass with up to 50% without increasing the effect of heating during sparking. Furthermore the length of the sample can be minimized and the sample has an excellent fixation in the first depression 27'. The lowered temperature of the sample reduces the temperature requirements of the sealing accordingly. The maximum temperature of the sample is creating the highest risk regarding components released from the sealing that might influence the analysis result.

FIGS. 4a and 4b show that the second depression 29' has a cross sectional profile that is concavely shaped as well. In further embodiments, the depth of the second depression 29' can also continually increases towards the first depression 27'.

FIG. 5a shows a schematic view of a housing 7" of a sample chamber 25" according to another embodiment of the invention, and FIG. 5b shows a cut through the housing 7" shown in FIG. 5a.

The shown housing 7" essentially corresponds to the housing as shown in FIGS. 4a and 4b, but distinguishes from the embodiment shown in FIGS. 4a and 4b in that the first depression 27" is defined by an elongated triangularly shaped indentation, and the second depression 29" is also defined by an by an elongated triangularly shaped indentation.

However, the person skilled in the art would know that other shapes, such as polygonal shapes, can be used instead to achieve similar results.

The features disclosed in the claims, the specification, and the drawings maybe essential for different embodiments of the claimed invention, both separately or in any combination with each other.

REFERENCE SIGNS

1 Sampler
3 Measuring Head
5 Carrier Tube
7, 7', 7" Sample Chamber Assembly
9 Housing
11 Cover Plate
13 Clamp
15 Immersion End of Measuring Head
16 Inlet Cap
17 Immersion End of Sample Chamber
18 Protection Cap
19 Inflow Conduit
21 Sealing Member
22 Adhesive
23', 23" First Face
25', 25" Sample Chamber
27', 27" First Depression
29', 29" Second Depression
I Immersion Direction
X Longitudinal Axis

The invention claimed is:

1. A sampler for taking samples from a molten metal bath, the sampler comprising:
 a carrier tube having an immersion end; and
 a sample chamber assembly arranged on the immersion end of the carrier tube, the sample chamber assembly comprising a cover plate and a housing, wherein the housing comprises:
  an immersion end having a first opening for an inflow conduit and an opposing end having a second opening for a gas coupler,
  a first face extending between the immersion end and the opposing end, the first face having a first depression proximate the immersion end and a second depression, the first depression being an analysis zone and the second depression being a ventilation zone, a portion of the analysis zone overlying a distribution zone which is in direct flow communication with the first opening and configured to receive a molten metal from the inflow conduit,
  wherein the first depression has a cross sectional profile perpendicular to a central longitudinal axis thereof, the cross sectional profile being concavely or triangularly shaped,
  wherein the cover plate and the housing are configured to be assembled together to form a sample cavity including the distribution zone, the analysis zone and the ventilation zone, such that an analysis surface of a solidified metal sample formed within the sample cavity lies in a first plane, and
  wherein the first and second openings are spaced apart from the first plane.

2. The sampler of claim 1, wherein the second depression has a cross sectional profile perpendicular to a central longitudinal axis thereof, the cross sectional profile being concavely or triangularly shaped, and wherein the depth of the second depression continually increases towards the first depression.

3. The sampler of claim 1, wherein the first depression has a substantially uniform depth, or an increasing depth towards the second depression or towards the immersion end.

4. The sampler of claim 1, wherein the sample cavity and the first and second openings are aligned along a common longitudinal axis.

5. The sampler of claim 1, wherein the analysis zone, the distribution zone and the ventilation zone are structured as a plurality of contiguous segments, each segment having a length to depth ratio, a sum of the length to depth ratios of the plurality of segments being greater than 25.

6. The sampler of claim 1, wherein the distribution zone, the analysis zone and the ventilation zone are structured as a plurality of contiguous segments, each segment having a length to depth ratio, the length to depth ratios of the segments successively increasing as the distance from the first opening increases.

7. The sampler of claim 1, wherein there are no increases in a width dimension of at least a portion of the analysis zone in a flow direction of the molten metal which extends from the end of the distribution zone toward the second opening.

8. The sampler of claim 1, wherein a total length of the analysis zone and the ventilation zone is between 20 and 50 mm.

9. The sampler of claim 1, wherein a cross-sectional area of the analysis zone gradually tapers in the flow direction of the molten metal, and
wherein a cross-sectional area of the ventilation zone gradually tapers in the flow direction of the molten metal.

10. The sampler of claim 1, wherein a total length of the analysis zone and the ventilation zone is about 30 mm.

11. The sampler of claim 1, wherein a cross-sectional area of the analysis zone gradually tapers in the flow direction of the molten metal, or wherein a cross-sectional area of the ventilation zone gradually tapers in the flow direction of the molten metal.

12. The sampler of claim 1, wherein the second depression has a cross sectional profile perpendicular to a central longitudinal axis thereof, the cross sectional profile being concavely or triangularly shaped, or wherein the depth of the second depression continually increases towards the first depression.

13. The sample of claim 1, wherein the molten metal is molten steel.

\* \* \* \* \*